United States Patent
Griffin et al.

(10) Patent No.: US 7,918,806 B2
(45) Date of Patent: *Apr. 5, 2011

(54) GUIDE WIRE WITH ADJUSTABLE FLEXIBILITY

(75) Inventors: Stephen Griffin, Sunnyvale, CA (US); Gregory E. Mirigian, Dublin, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 442 days.

This patent is subject to a terminal disclaimer.

(21) Appl. No.: 11/352,753

(22) Filed: Feb. 13, 2006

(65) Prior Publication Data

US 2006/0127561 A1    Jun. 15, 2006

Related U.S. Application Data

(63) Continuation of application No. 10/025,428, filed on Dec. 18, 2001, now Pat. No. 7,018,346.

(51) Int. Cl.
*A61M 25/00*    (2006.01)

(52) U.S. Cl. ..................................................... 600/585

(58) Field of Classification Search .......... 600/433–435, 600/585; 604/164.13, 170.01, 171; 606/28
See application file for complete search history.

(56) References Cited

U.S. PATENT DOCUMENTS

| | | |
|---|---|---|
| 3,416,531 A | 12/1968 | Edwards |
| 3,485,234 A | 12/1969 | Stevens |
| 3,612,038 A | 10/1971 | Halligan |
| 3,612,058 A | 10/1971 | Ackerman |
| 3,725,116 A | 4/1973 | Parker et al. |
| 4,210,478 A | 7/1980 | Shoney |
| 4,292,270 A | 9/1981 | Hannah et al. |
| 4,341,218 A | 7/1982 | U |
| 4,359,453 A | 11/1982 | Gordon |
| 4,369,206 A | 1/1983 | Mayer et al. |
| 4,385,635 A | 5/1983 | Ruiz |
| 4,419,095 A | 12/1983 | Nebergall et al. |
| 4,427,000 A | 1/1984 | Ueda |

(Continued)

FOREIGN PATENT DOCUMENTS

EP    0 277 366    8/1988

(Continued)

OTHER PUBLICATIONS

Gleich, Bernhard, "Catheter Temperature Measurement with Ferromagnets," *Research Disclosure*, Feb. 2001, p. 189.

(Continued)

*Primary Examiner* — Max Hindenburg
*Assistant Examiner* — Jonathan M Foreman
(74) *Attorney, Agent, or Firm* — Seager, Tufte & Wickhem, LLC

(57) ABSTRACT

A guide wire with a distal portion having adjustable flexibility. The guide wire may include a distal polymeric member and a heat source. The heat source may be activated to cause the polymeric member to increase in temperature and increase in flexibility. The increase in flexibility of the distal portion of the guide wire enhances the ability of the guide wire to navigate tortuous vasculature to a target site. After the guide wire has been navigated to the target site, the heat source may be deactivated to cause the polymeric member to decrease in temperature and increase in stiffness. The increase in stiffness of the distal portion of the guide wire enhances support provided for devices (e.g., catheters) advanced thereon.

11 Claims, 1 Drawing Sheet

U.S. PATENT DOCUMENTS

| | | | |
|---|---|---|---|
| 4,516,970 A | 5/1985 | Kaufman et al. | |
| 4,516,972 A | 5/1985 | Samson | |
| 4,531,943 A | 7/1985 | Van Tassel et al. | |
| 4,563,181 A | 1/1986 | Wijayarathna et al. | |
| 4,588,399 A | 5/1986 | Nebergall et al. | |
| 4,590,922 A | 5/1986 | Gordon | |
| 4,622,953 A | 11/1986 | Gordon | |
| 4,627,436 A | 12/1986 | Leckrone | |
| 4,636,346 A | 1/1987 | Gold et al. | |
| 4,643,186 A | 2/1987 | Rosen et al. | |
| 4,654,024 A | 3/1987 | Crittenden et al. | |
| 4,655,771 A | 4/1987 | Wallsten | |
| 4,672,962 A | 6/1987 | Hershenson | |
| 4,685,458 A | 8/1987 | Leckrone | |
| 4,690,175 A | 9/1987 | Ouchi et al. | |
| 4,705,511 A | 11/1987 | Kocak | |
| 4,728,322 A | 3/1988 | Walker et al. | |
| 4,735,620 A | 4/1988 | Ruiz | |
| 4,735,796 A | 4/1988 | Gordon | |
| 4,740,674 A * | 4/1988 | Tsutsumi | 219/523 |
| 4,747,405 A | 5/1988 | Leckrone | |
| 4,748,979 A | 6/1988 | Hershenson | |
| 4,753,223 A | 6/1988 | Bremer | |
| 4,767,611 A | 8/1988 | Gordon | |
| 4,790,311 A | 12/1988 | Ruiz | |
| 4,807,620 A | 2/1989 | Strul et al. | |
| 4,817,613 A | 4/1989 | Jaraczewski et al. | |
| 4,838,859 A | 6/1989 | Strassmann | |
| 4,838,879 A | 6/1989 | Tanabe et al. | |
| 4,840,622 A | 6/1989 | Hardy | |
| 4,842,590 A | 6/1989 | Tanabe et al. | |
| 4,863,442 A | 9/1989 | DeMello et al. | |
| 4,869,248 A | 9/1989 | Narula | |
| 4,895,168 A * | 1/1990 | Machek | 600/585 |
| 4,898,591 A | 2/1990 | Jang et al. | |
| 4,899,787 A | 2/1990 | Ouchi et al. | |
| 4,923,437 A | 5/1990 | Gordon | |
| 4,930,494 A | 6/1990 | Takehana et al. | |
| 4,950,258 A | 8/1990 | Kawai et al. | |
| 4,981,478 A | 1/1991 | Evard et al. | |
| 4,984,581 A | 1/1991 | Stice | |
| 5,009,655 A | 4/1991 | Daignault, Jr. et al. | |
| 5,017,259 A | 5/1991 | Kohsai | |
| 5,019,040 A | 5/1991 | Itaoka et al. | |
| 5,025,799 A | 6/1991 | Wilson | |
| 5,041,089 A | 8/1991 | Mueller et al. | |
| 5,047,025 A | 9/1991 | Taylor et al. | |
| 5,055,101 A | 10/1991 | McCoy | |
| 5,057,092 A | 10/1991 | Webster, Jr. | |
| 5,069,674 A | 12/1991 | Fearnot et al. | |
| 5,078,702 A | 1/1992 | Pomeranz | |
| 5,087,256 A | 2/1992 | Taylor et al. | |
| 5,090,956 A | 2/1992 | McCoy | |
| 5,093,385 A | 3/1992 | Ali | |
| 5,098,429 A | 3/1992 | Sterzer | |
| 5,116,317 A | 5/1992 | Carson et al. | |
| 5,143,085 A | 9/1992 | Wilson | |
| 5,156,596 A | 10/1992 | Balbierz et al. | |
| 5,160,559 A | 11/1992 | Scovil et al. | |
| 5,163,431 A | 11/1992 | Griep | |
| 5,176,660 A | 1/1993 | Truckai | |
| 5,180,376 A | 1/1993 | Fischell | |
| 5,190,520 A | 3/1993 | Fenton, Jr. et al. | |
| 5,190,540 A | 3/1993 | Lee | |
| 5,203,772 A | 4/1993 | Hammerslag et al. | |
| 5,211,183 A | 5/1993 | Wilson | |
| 5,217,440 A | 6/1993 | Frassica | |
| 5,221,270 A | 6/1993 | Parker | |
| 5,221,372 A | 6/1993 | Olson | |
| 5,222,949 A | 6/1993 | Kaldany | |
| 5,234,416 A | 8/1993 | Macaulay et al. | |
| 5,249,585 A | 10/1993 | Turner et al. | |
| 5,254,107 A | 10/1993 | Soltesz | |
| 5,257,635 A | 11/1993 | Langberg | |
| 5,279,596 A | 1/1994 | Castaneda et al. | |
| 5,290,230 A | 3/1994 | Ainsworth et al. | |
| 5,298,532 A | 3/1994 | Ali | |
| 5,306,252 A | 4/1994 | Yutori et al. | |
| 5,308,342 A | 5/1994 | Sepetka et al. | |
| 5,318,999 A | 6/1994 | Mitra et al. | |
| 5,334,168 A | 8/1994 | Hemmer | |
| 5,335,305 A | 8/1994 | Kosa et al. | |
| 5,344,444 A | 9/1994 | Glastra | |
| 5,349,946 A | 9/1994 | McComb | |
| 5,349,964 A | 9/1994 | Imran et al. | |
| 5,358,493 A | 10/1994 | Schweich, Jr. et al. | |
| 5,368,591 A | 11/1994 | Lennox et al. | |
| 5,370,109 A | 12/1994 | Cuny | |
| 5,423,773 A | 6/1995 | Jimenez | |
| 5,423,774 A | 6/1995 | Fischell et al. | |
| 5,433,200 A | 7/1995 | Fleischhacker, Jr. | |
| 5,441,489 A | 8/1995 | Utsumi et al. | |
| 5,443,495 A | 8/1995 | Buscemi et al. | |
| 5,445,624 A | 8/1995 | Jimenez | |
| 5,449,369 A | 9/1995 | Imran | |
| 5,449,703 A | 9/1995 | Mitra et al. | |
| 5,464,419 A | 11/1995 | Glastra | |
| 5,497,786 A | 3/1996 | Urick | |
| 5,502,087 A | 3/1996 | Tateosian et al. | |
| 5,509,910 A | 4/1996 | Lunn | |
| 5,511,547 A | 4/1996 | Markle et al. | |
| 5,514,108 A | 5/1996 | Stevens | |
| 5,529,653 A | 6/1996 | Glastra | |
| 5,531,685 A | 7/1996 | Hemmer et al. | |
| 5,531,715 A | 7/1996 | Engelson et al. | |
| 5,538,512 A | 7/1996 | Zenzon et al. | |
| 5,545,151 A | 8/1996 | O'Connor et al. | |
| 5,569,218 A | 10/1996 | Berg | |
| 5,578,008 A | 11/1996 | Hara | |
| 5,591,199 A | 1/1997 | Porter et al. | |
| 5,599,319 A | 2/1997 | Stevens | |
| 5,603,705 A | 2/1997 | Berg | |
| 5,626,136 A | 5/1997 | Webster, Jr. | |
| 5,658,263 A | 8/1997 | Dang et al. | |
| 5,662,621 A | 9/1997 | Lafontaine | |
| 5,662,622 A | 9/1997 | Gore et al. | |
| 5,665,063 A | 9/1997 | Roth et al. | |
| 5,674,208 A | 10/1997 | Berg et al. | |
| 5,676,659 A | 10/1997 | McGurk | |
| 5,711,909 A | 1/1998 | Gore et al. | |
| 5,766,204 A | 6/1998 | Porter et al. | |
| 5,769,796 A | 6/1998 | Palermo et al. | |
| 5,772,628 A | 6/1998 | Bacich et al. | |
| 5,779,673 A | 7/1998 | Roth et al. | |
| 5,792,401 A | 8/1998 | Burnham | |
| 5,800,500 A | 9/1998 | Spelman et al. | |
| 5,810,867 A | 9/1998 | Zarbatany et al. | |
| 5,810,874 A | 9/1998 | Lefebvre | |
| 5,830,224 A | 11/1998 | Cohn et al. | |
| 5,836,925 A | 11/1998 | Soltesz | |
| 5,891,082 A | 4/1999 | Leone et al. | |
| 5,891,094 A | 4/1999 | Masterson et al. | |
| 5,897,537 A | 4/1999 | Berg et al. | |
| 5,911,715 A | 6/1999 | Berg et al. | |
| 5,911,737 A | 6/1999 | Lee et al. | |
| 5,938,623 A | 8/1999 | Quiachon et al. | |
| 5,951,495 A | 9/1999 | Berg et al. | |
| 5,954,651 A | 9/1999 | Berg et al. | |
| 5,957,966 A | 9/1999 | Schroeppel et al. | |
| 5,971,979 A | 10/1999 | Joye et al. | |
| 5,997,526 A | 12/1999 | Giba et al. | |
| 5,997,570 A | 12/1999 | Ligtenberg et al. | |
| 6,006,756 A | 12/1999 | Shadduck | |
| 6,017,323 A | 1/2000 | Chee | |
| 6,017,335 A | 1/2000 | Burnham | |
| 6,027,450 A | 2/2000 | Brown et al. | |
| 6,030,405 A | 2/2000 | Zarbatany et al. | |
| 6,042,578 A | 3/2000 | Dinh et al. | |
| 6,056,844 A | 5/2000 | Guiles et al. | |
| 6,059,815 A | 5/2000 | Lee et al. | |
| 6,072,154 A | 6/2000 | Maynard | |
| 6,076,609 A | 6/2000 | Job | |
| 6,086,599 A | 7/2000 | Lee et al. | |
| 6,090,099 A | 7/2000 | Samson et al. | |
| 6,102,917 A | 8/2000 | Maitland et al. | |
| 6,102,933 A | 8/2000 | Lee et al. | |
| 6,123,718 A | 9/2000 | Tu et al. | |

| | | |
|---|---|---|
| 6,165,166 A | 12/2000 | Samuelson et al. |
| 6,179,824 B1 | 1/2001 | Eggers et al. |
| 6,183,443 B1 | 2/2001 | Kratoska et al. |
| 6,197,844 B1 | 3/2001 | Hamrock et al. |
| 6,210,393 B1 | 4/2001 | Brisken |
| 6,212,422 B1 | 4/2001 | Berg et al. |
| 6,224,610 B1 | 5/2001 | Ferrera |
| 6,240,231 B1 | 5/2001 | Ferrera et al. |
| 6,258,195 B1 | 7/2001 | Holman et al. |
| 6,272,371 B1 | 8/2001 | Shlomo |
| 6,287,320 B1 | 9/2001 | Slepian |
| 6,290,692 B1 | 9/2001 | Klima et al. |
| 6,296,622 B1 | 10/2001 | Kurz et al. |
| 6,323,251 B1 | 11/2001 | Perez et al. |
| 6,355,029 B1 | 3/2002 | Joye et al. |
| 6,387,052 B1 | 5/2002 | Quinn et al. |
| 6,388,043 B1 | 5/2002 | Langer et al. |
| 6,428,534 B1 | 8/2002 | Joye et al. |
| 6,428,563 B1 | 8/2002 | Keller |
| 6,468,297 B1 | 10/2002 | Williams et al. |
| 6,485,512 B1 | 11/2002 | Cheng |
| 6,520,952 B1 | 2/2003 | Jimenez |
| 6,533,752 B1 | 3/2003 | Waram et al. |
| 6,555,288 B1 | 4/2003 | Xu et al. |
| 6,562,021 B1 | 5/2003 | Derbin et al. |
| 6,579,913 B2 | 6/2003 | Klinkenberg et al. |
| 6,598,280 B1 | 7/2003 | Giba et al. |
| 6,720,402 B2 | 4/2004 | Langer et al. |
| 6,740,094 B2 | 5/2004 | Maitland et al. |
| 6,740,107 B2 | 5/2004 | Loeb et al. |
| 7,018,346 B2 * | 3/2006 | Griffin et al. ............... 600/585 |
| 7,351,199 B2 | 4/2008 | Nash |
| 2001/0039412 A1 | 11/2001 | Fariabi |
| 2002/0026182 A1 | 2/2002 | Joye et al. |
| 2002/0095169 A1 | 7/2002 | Maitland et al. |
| 2002/0165520 A1 | 11/2002 | Forman |
| 2003/0069522 A1 | 4/2003 | Jacobsen et al. |
| 2003/0114914 A1 | 6/2003 | Cheng |
| 2003/0125710 A1 | 7/2003 | Pepin |
| 2004/0054301 A1 | 3/2004 | Cassell |
| 2004/0104512 A1 | 6/2004 | Eidenschink |
| 2008/0009831 A1 | 1/2008 | Griffin |

FOREIGN PATENT DOCUMENTS

| | | |
|---|---|---|
| EP | 0 382 974 | 8/1990 |
| EP | 0 417 865 | 3/1991 |
| EP | 0 420 993 | 4/1991 |
| EP | 0 473 045 | 3/1992 |
| EP | 0 180 348 | 5/1992 |
| EP | 0 555 088 | 8/1993 |
| JP | 4-40652 U | 4/1992 |
| JP | 5-84303 A | 4/1993 |
| JP | 10-156942 A | 6/1998 |
| WO | WO 86/03980 | 7/1986 |
| WO | WO 92/15356 | 9/1992 |
| WO | WO 93/15785 | 8/1993 |
| WO | WO 95/10321 | 4/1995 |
| WO | WO 9510321 | 4/1995 |
| WO | WO 95/29722 | 11/1995 |
| WO | WO 96/20750 | 7/1996 |
| WO | WO 97/14466 | 4/1997 |
| WO | WO 00/03756 | 1/2000 |
| WO | WO 02/078777 | 10/2002 |

OTHER PUBLICATIONS

Kolobow et al., "A New Thin-Walled Nonkinking Catheter for Peripheral Vascular Connulation," *Surgery*, vol. 68, No. 4, Oct. 1970, pp. 625-626.

Suwanwatana, W., Research Poster—University of Delaware "Inductions Heating of Thin Films Containing Ferromagnetic Particles", www.ccm.udel.edu/publications/AR/posters/PS/Suwanwatana, Mar. 18, 2002, 2 pages.

* cited by examiner

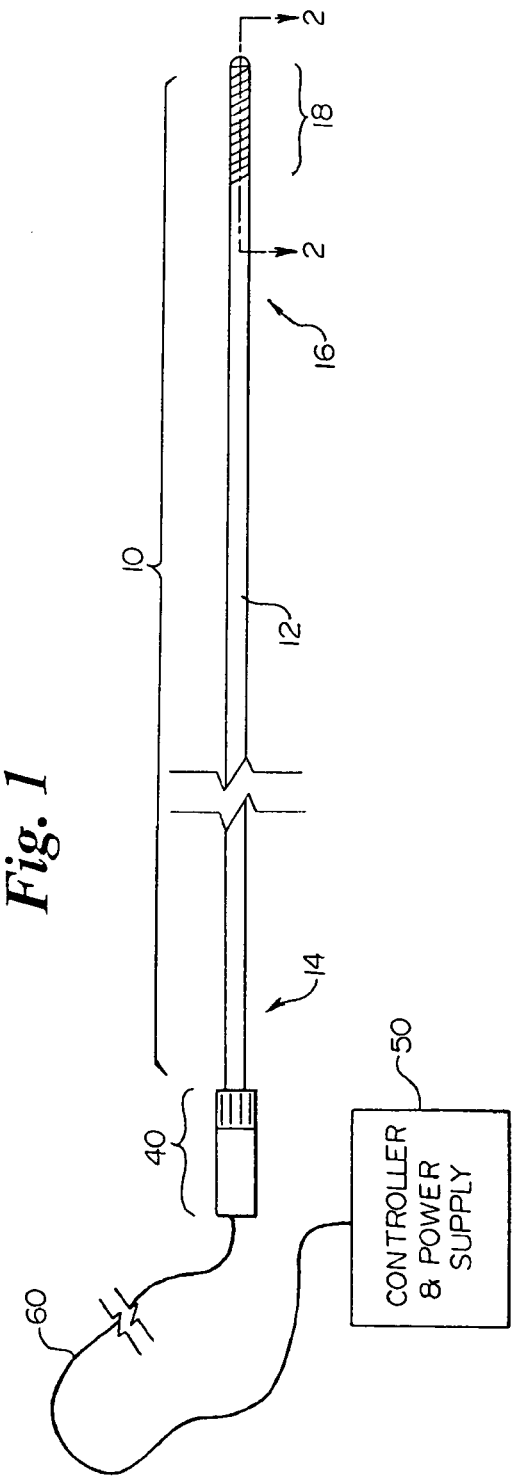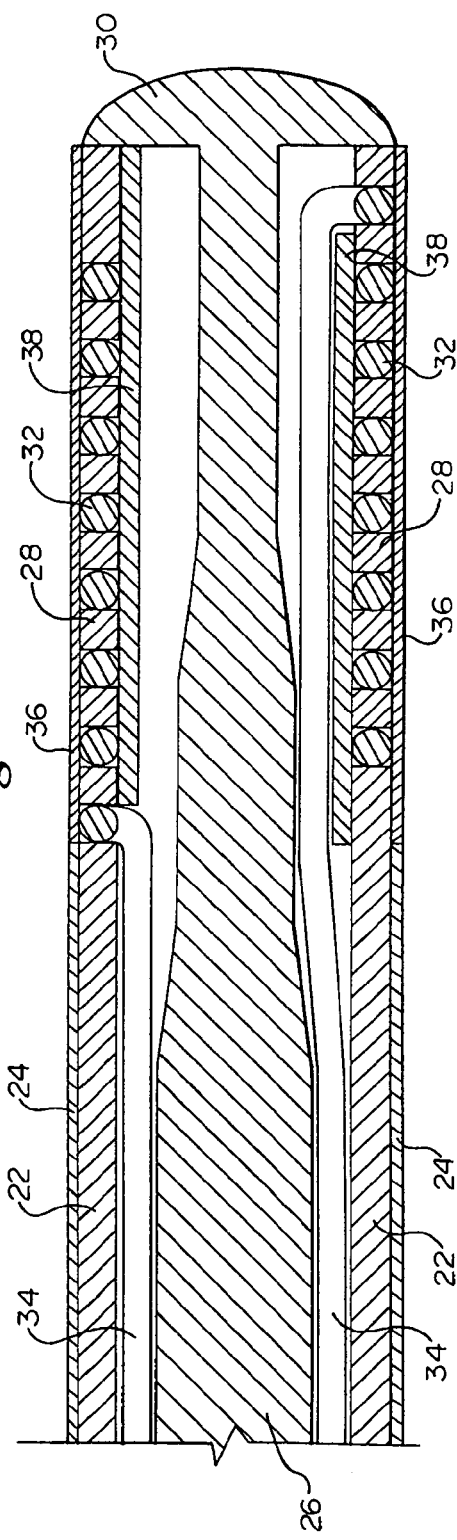

GUIDE WIRE WITH ADJUSTABLE FLEXIBILITY

CROSS REFERENCE TO CO-PENDING APPLICATIONS

This application is a continuation of U.S. patent application Ser. No. 10/025,428, filed Dec. 18, 2001 now U.S. Pat. No. 7,018,346.

FIELD OF THE INVENTION

The present invention generally relates to intravascular guide wires. In particular, the present invention relates to intravascular guide wires having adjustable flexibility.

BACKGROUND OF THE INVENTION

Intravascular guide wires are often used to facilitate the delivery of therapeutic and diagnostic devices to remote vascular sites in the human body. In particular, intravascular guide wires are used to navigate through a patient's vasculature from a convenient location outside the patient's body, to a target site inside the patient's body requiring diagnosis and/or therapy. Once access to the target site has been provided by the guide wire, a therapeutic or diagnostic device (e.g., catheter) may then be advanced over the guide wire to the target site, and the desired therapeutic or diagnostic steps may be performed.

To facilitate navigation in tortuous vasculature, it is desirable that the guide wire have a relatively flexible distal end. To provide good support for devices advanced over the guide wire, it is desirable that the guide wire have a relatively stiff distal end. Conventional guide wires typically address these competing needs by establishing a compromise in flexibility and stiffness. However, it would be desirable to have a guide wire that does not compromise these competing needs.

SUMMARY OF THE INVENTION

To address these needs, the present invention provides, in one exemplary embodiment, a guide wire that has a distal portion with adjustable flexibility. In one example, the guide wire includes a distal polymeric member and a heat source. The heat source may be activated by a power supply, which causes the polymeric member to increase in temperature, to thereby increase the flexibility of the distal portion of the guide wire. The polymeric member may comprise a shape memory polymer having a glass transition temperature, wherein the increase in temperature is across the glass transition temperature.

The increase in flexibility of the distal portion of the guide wire enhances the ability of the guide wire to navigate vasculature of varying degrees of tortuosity. After the guide wire has been navigated to the target site, the heat source may be deactivated, which causes the polymeric member to decrease in temperature, to thereby increase the stiffness of the distal portion of the guide wire and provide enhanced support for devices advanced thereon.

BRIEF DESCRIPTION OF THE DRAWINGS

FIG. 1 is a plan view of a guide wire system, including a guide wire, a controller/power source and a coupling/lead therebetween, in accordance with an exemplary embodiment of the present invention; and FIG. 2 is a longitudinal cross-sectional view taken along line 2-2 in FIG. 1, illustrating in detail the distal portion of the guide wire shown in FIG. 1.

DETAILED DESCRIPTION

The following description should be read with reference to the drawings wherein like reference numerals indicate like elements throughout the several views. The detailed description and drawings illustrate embodiments by way of example, not limitation.

Refer now to FIG. 1 which illustrates a guide wire system in accordance with an exemplary embodiment of the present invention. The guide wire system includes a guide wire 10 connected to a controller and power source 50 by a coupling 40 and lead 60.

Guide wire 10 includes an elongate shaft 12 having a proximal portion 14 and a distal portion 16. Distal portion 16 includes a soft atraumatic tip 18. The proximal portion 14 of the shaft 12 is relatively stiff to provide pushability and torquability, and the distal portion 16 has adjustable flexibility to provide trackability in navigating tortuous vasculature and support for devices advanced thereover.

Except as described herein and implicit in the drawings, the guide wire 10 may have conventional dimensions and may be formed of conventional materials using conventional techniques known for intravascular guide wires used to navigate the human vasculature to remote locations including, but not limited to, the neurovasculature, the coronary vasculature, and the peripheral vasculature.

As will be discussed in more detail with reference to FIG. 2, the distal portion 16 of the guide wire 10 includes a heat source that is thermally connected to a polymeric member that increases in flexibility when heated, and increases in stiffness (e.g., returns to its nominal flexibility or stiffness at body temperature) when cooled. Thus, by activating or deactivating the heat source, the flexibility of the polymeric member, and thus the flexibility of the distal portion 16, may be adjusted. For example, the flexibility of the distal portion 16 may be increased by activating the heat source, which enhances the ability of the guide wire 10 to navigate tortuous vasculature to a target site. After the guide wire 10 has been navigated to the desired target site, the heat source may be deactivated to cause the distal portion 16 to increase in stiffness, which enhances guide wire 10 support provided for devices (e.g., catheters) advanced thereon.

To control activation and deactivation of the heat source, a controller/power supply 50 is connected by lead 60 to a coupling 40 which is releasably and rotatably connected to the proximal portion 14 of the guide wire shaft 12. Controller/power supply 50 may comprise a conventional power supply with conventional control circuitry to provide a constant or modulated AC or DC signal. The signal is transmitted by lead 60, which may comprise two (or more) conductors. The conductors in the lead 60 may be connected to leads in the shaft 12 of the guide wire by coupling 40. Coupling 40 may be removable to permit devices such as catheters to be advanced over the proximal end of the guide wire 10. Coupling 40 may also be rotatable to permit the guide wire to be rotated and steered during intravascular navigation.

Refer now to FIG. 2 which illustrates in detail certain aspects of the distal portion 16 of the guide wire 10, which may be in common with certain aspects of the proximal portion 14. As seen in FIG. 2, the shaft 12 includes a hypotube 22 which may comprise, for example, stainless steel or a super elastic metal such as a nickel titanium alloy, Nitinol, MP35N, Inconel, etc. The hypotube 22 may extend from the proximal end of the guide wire shaft 12, and may include an outer sleeve 24 comprising a polymer such as polyurethane. A tapered core wire 26 may extend through the lumen in the hypotube 22, and may comprise stainless steel or a super elastic metal such as a nickel titanium alloy, Nitinol, MP35N, Inconel, etc. The distal end of the hypotube 22 in the region of the distal tip 18 may be helically slotted 28 to enhance flexibility. The distal end of the core wire 26 may be welded to the distal end of the slotted portion 28 of the hypotube 22 to form an atraumatic weld ball 30.

As mentioned previously, the distal portion 16 of the guide wire shaft 12 includes a heat source. In this particular example, the heat source comprises a resistive element 32. Resistive element 32 may comprise a tungsten or steel alloy that may be formed into a coil and heated by electro-resistive heating. Heater coil 32 may be disposed between adjacent turns in the slotted portion 28 of the hypotube 22. The resistive heater coil 32 is connected to insultated leads 34 which may be disposed in the lumen of the hypotube 22 around the core wire 26. Leads 34 are connected to coupling 40, which in turn is connected to controller/power supply 50 via lead 60.

A polymeric outer tube 36 may be disposed about the resistive heater coil 32, and a polymeric inner tube 38 may be provided to support the heater coil 32. The polymeric outer tube 36 and/or the polymeric inner tube 38 may be formed of a polymer that changes in stiffness when heated. For example, the polymeric outer tube 36 and/or the polymeric inner tube 38 may be formed of a polymer that is relatively stiff at temperatures at or below body temperature (37° C. or less) and relatively flexible at temperatures above body temperature. For example, a polymer may be selected with a glass transition temperature ($T_g$) that is above body temperature, such that heating the polymer above $T_g$ results in the distal portion 16 of the guide wire 10 becoming relatively more flexible, and cooling the polymer below $T_g$, even when the guide wire 10 is disposed in the patient's body, results in the distal portion 16 of the guide wire 10 becoming relatively more stiff. In a preferred embodiment, the polymeric outer tube 36 and/or the polymeric inner tube 38 may be formed of a shape memory polymer (SMP) such as a shape memory polyurethane available from Mitsubishi. Other examples of suitable SMPs include polynorbornenes, polycaprolactones and copolymers thereof available from Pnemoscience. Some SMPs, such as polynorbornene, may change flexibility without changing temperature across $T_g$. Such SMPs may be above $T_g$ at room temperature or body temperature, and may exhibit SMP characteristics at or near the melt temperature ($T_m$).

It should be understood that this disclosure is, in many respects, only illustrative. Changes may be made in details, particularly in matters of shape, size, arrangement of parts and order of steps without departing from the scope of the invention. The invention's scope is, of course, defined in the language in which the appended claims are expressed.

What is claimed is:

1. A method for manufacturing a guidewire, the method comprising:
   providing a tubular shaft having an inner surface, an outer surface, and a helically slotted portion;
   disposing a heat source on the shaft, wherein the heat source includes a coil at least partially disposed in the helically slotted portion;
   attaching a polymeric member to the outer surface of the shaft about the heat source, the polymeric member being in thermal communication with the heat source and having a first flexibility at a first temperature and a second flexibility at a second temperature; and
   attaching a second polymeric member to the inner surface.

2. The method of claim 1, wherein the heat source includes an outer surface and wherein at least a portion of the polymeric member is attached to the outer surface of the heat source.

3. The method of claim 1, wherein the polymeric member includes a shape memory polymer.

4. The method of claim 1, wherein the heat source includes a resistive heating element.

5. A guidewire manufactured by the method of claim 1.

6. A method for manufacturing a guidewire, the method comprising:
   providing a shaft having an outer surface;
   wherein the shaft includes a hypotube having a lumen therethrough and a core wire disposed within the lumen;
   attaching the distal end of the core wire to the distal end of the hypotube;
   disposing a heat source on the shaft, wherein the heat source includes a coil;
   wherein at least a portion of the heat source is in contact with at least a portion of the shaft;
   wherein the hypotube includes a helically slotted portion and wherein at least a portion of the coil is disposed in the helically slotted portion; and
   attaching a polymeric member to the outer surface of the shaft about the heat source, the polymeric member being in thermal communication with the heat source and having a first flexibility at a first temperature and a second flexibility at a second temperature.

7. The method of claim 6, wherein the heat source includes an outer surface and wherein at least a portion of the polymeric member is attached to the outer surface of the heat source.

8. The method of claim 6, wherein the polymeric member includes a shape memory polymer.

9. A guidewire manufactured by the method of claim 6.

10. A method for manufacturing a guidewire, the method comprising:
    providing a tubular shaft having an outer surface, a lumen extending through the shaft from a proximal end to a distal end thereof, the lumen defining an inner surface, and a helically slotted portion formed in the distal end;
    disposing a heater coil between adjacent turns in the helically slotted portion;
    wherein at least a portion of the heater coil is in contact with at least a portion of the shaft, and wherein the heater coil is connected to insulated leads disposed within the lumen;
    disposing a core wire within the lumen;
    attaching the distal end of the core wire to the distal end of the shaft; and
    coupling a polymeric member to the outer surface of the shaft about the heat source, the polymeric member being in thermal communication with the heater coil and having a first flexibility at a first temperature and a second flexibility at a second temperature;
    coupling a second polymeric member to the inner surface of the shaft, the second polymeric member being in thermal communication with the heater coil;
    wherein the second polymeric member supports the heater coil.

11. A guidewire manufactured by the method of claim 10.

* * * * *